(12) United States Patent
Mueller-Boetticher et al.

(10) Patent No.: US 6,495,694 B2
(45) Date of Patent: Dec. 17, 2002

(54) EFFICIENT SEPARATION OF ENANTIOMERS OF PIPERIDONE DERIVATIVES BY PRECIPITATION OF THE DESIRED EANTIOMER DURING IN SITU RACEMIZATION OF THE UNWANTED ENANTIOMER

(75) Inventors: Hermann Mueller-Boetticher, Ober-Hilbersheim (DE); Gerd-Rainer Bressler, Bingen (DE); Paul Kreye, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/843,061

(22) Filed: Apr. 26, 2001

(65) Prior Publication Data

US 2002/0010336 A1 Jan. 24, 2002

Related U.S. Application Data

(60) Provisional application No. 60/216,003, filed on Jul. 3, 2000.

(30) Foreign Application Priority Data

Jun. 16, 2000 (DE) .......................... 100 29 851

(51) Int. Cl.$^7$ ............................ C07D 211/44
(52) U.S. Cl. ................. 546/216; 546/192; 546/207; 546/208
(58) Field of Search ................ 546/192, 207, 546/208, 225, 216

(56) References Cited

U.S. PATENT DOCUMENTS 4,406,904 A * 9/1983 Welle et al. ................. 424/260
4,425,353 A * 1/1984 Akkerman et al. .......... 424/267
5,945,535 A * 8/1999 Grauert et al. ................ 546/97

FOREIGN PATENT DOCUMENTS

DE 195 28 472 A1 2/1997
WO WO 96/09290 A1 3/1996

* cited by examiner

Primary Examiner—Alan L. Rotman
Assistant Examiner—Rita Desai
(74) Attorney, Agent, or Firm—Robert P. Raymond; Timothy X. Witkowski; Mary-Ellen Devlin

(57) ABSTRACT

A process for dynamically separating the enantiomers of a piperidone derivative of formula (1)

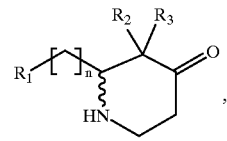

(1)

wherein:
  $R_1$ is aryl optionally mono- to polysubstituted, heteroaryl, which is linked to the chiral center via at least one carbon atom of its own or a carbon atom belonging to the methylene bridge, or straight-chain or branched $C_1$–$C_8$-alkyl optionally mono- to polysubstituted by halogen;
  $R_2$ and $R_3$, which are identical or different, are each straight-chain or branched $C_1$–$C_6$-alkyl; and
  n is 0, 1, 2 or 3,
the process comprising:
(a) dissolving an optically active acid and optionally catalytic amounts of a sulfonic acid in a solvent to make a first solution maintained at a desired temperature;
(b) adding a second solution of the piperidone derivative to the first solution to precipitate out the desired enantiomer of the piperidone derivative as a salt of the optically active acid used while racemizing the unwanted enantiomer of the piperidone derivative in solution and further precipitating the desired enantiomer of the piperidone derivative from the racemizing the unwanted enantiomer of the piperidone derivative in a dynamic process; and
(c) separating the desired enantiomer of the piperidone derivative as a salt of the optically active acid.

23 Claims, No Drawings

EFFICIENT SEPARATION OF ENANTIOMERS OF PIPERIDONE DERIVATIVES BY PRECIPITATION OF THE DESIRED EANTIOMER DURING IN SITU RACEMIZATION OF THE UNWANTED ENANTIOMER

RELATED APPLICATIONS

Benefit under 35 U.S.C. § 119(e) of prior U.S. provisional Ser. No. 60/216,003, filed Jul. 3, 2000, is hereby claimed.

FIELD OF THE INVENTION

The invention relates to a process which can be used on an industrial scale for dynamically separating the enantiomers of piperidone derivatives of general formula (1)

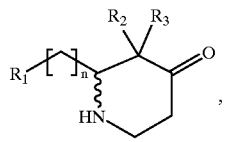

(1)

wherein $R_1$, $R_2$, $R_3$, and n have the meanings given in the specification and claims, with simultaneous racemization in situ of the unreacted enantiomer.

BACKGROUND OF THE INVENTION

Enantiomerically pure piperidone derivatives of general formula (1), wherein
$R_1$ denotes

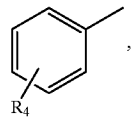

$R_2$ and $R_3$ each denote a methyl group,
$R_4$ denotes hydrogen, $C_1$–$C_6$-alkyl, halogen, hydroxy, $C_1$–$C_8$-alkoxy, a benzoyl group bound via an oxygen or an alkylcarbonyl group having a straight-chain or branched lower alkyl group with 1 to 6 carbon atoms, wherein the alkyl group may optionally be substituted by one or more halogen atom(s), which may be identical to or different from one another, nitro, cyano, amino, amino mono- or disubstituted by $C_1$–$C_8$-alkyl, wherein the alkyl groups may be identical or different, —NH-acyl-($C_1$–$C_8$-alkyl), wherein acyl denotes benzoyl or an alkylcarbonyl group having a straight-chain or branched lower alkyl group with 1 to 6 carbon atoms, whilst the alkyl group may optionally be substituted by one or more halogen atom(s), which may be identical to or different from each other, or a group which may be converted into one of the above-mentioned groups by simple reactions known per se, and
n denotes 1,
are of major importance as intermediate products for the preparation of pharmaceutically valuable benzomorphan derivatives which may be used, for example, in the treatment of neurodegenerative disorders and cerebral ischaemias such as cardiac infarct or cerebral stroke.

Processes for preparing enantiomerically enriched piperidone derivatives are known from the prior art. Published German application DE 195 28 472 describes a process which is essential to the invention, in which the desired enantiomer is precipitated from the solution of a mixture of enantiomeric 3,3-dimethyl-4-piperidones by reacting with a suitable organic acid, e.g., tartaric acid, as a salt, i.e., as the tartrate, for example. After separation of the crystals formed, the unwanted enantiomer contained in the mother liquor can be racemized by heating. After various purification processes and changes of the solvent, the desired enantiomer thus formed is again precipitated as described above and isolated. The process can be repeated several times.

This procedure known from the prior art makes it possible to increase the yield to 75%, i.e., to values which are significantly higher than the maximum yield of 50%, which is the maximum theoretical yield for racemate separation. This reduces the waste of materials and increases the efficiency of the synthesis.

The procedure disclosed in DE 195 28 472 comprising crystallization, separation of the crystals from the mother liquor, thermal re-racemization, crystallization, etc., however, is time-consuming and labor-intensive.

To reduce the extra work involved in purification and isolation and to save time and money, it is, particularly for large-scale industrial manufacture, desirable to have a process which carries out enantiomer separation as a dynamic one-pot process.

It is therefore the aim and problem of the present invention to overcome the disadvantages of the known process as described above by providing a process which can be used on an industrial scale, enabling the precipitation of the desired enantiomer and the racemization of the other enantiomer to be carried out in one step.

DETAILED DESCRIPTION OF THE INVENTION

Surprisingly, it has now been found that the separation of enantiomeric piperidone derivatives and the racemization of the unwanted enantiomer can be carried out simultaneously in one and the same reaction vessel and in one reaction step. The disadvantages of the process known from the prior art can thereby be avoided and the advantage of having a yield of more than 50% for the racemate separation, however, is unaffected or this yield may even be increased.

Consequently, the present invention relates to a process suitable for use on an industrial scale for separating the enantiomers of piperidone derivatives of general formula (1)

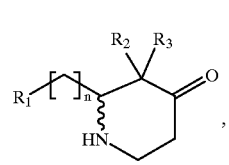

(1)

wherein
$R_1$ denotes $C_1$–$C_8$-alkyl, preferably $C_1$–$C_6$-alkyl, which may be straight-chain or branched and is optionally mono- to polysubstituted by halogen, aryl, which may optionally be mono- to polysubstituted, preferably optionally substituted phenyl or naphthyl, particularly preferably a group of general formula

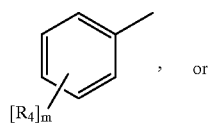, or heteroaryl, preferably pyridine, wherein the heterocyclic group is linked to the chiral center by a carbon atom belonging to the ring or originating from the methylene bridge, $R_2$ and $R_3$, which may be identical or different, denote $C_1$–$C_6$-alkyl, which may be straight-chain or branched, preferably methyl or ethyl, particularly preferably methyl;

$R_4$ independently of one another denote methoxy, ethoxy, isopropyloxy, halogen, hydroxy, $C_1$–$C_6$-alkyl, which may be partially or fully halogenated, such as, e.g., trifluoromethyl, amino, nitro, cyano, benzoyl, $C_1$–$C_6$-alkylcarbonyl, preferably methoxy;

n denotes 0, 1, 2 or 3, preferably 1, and m denotes 0, 1, 2 or 3, preferably 0 or 1, by crystallization of the desired enantiomer as a salt of a suitable organic acid with simultaneous racemization of the dissolved enantiomer.

In the process according to the invention for obtaining one enantiomer from a mixture of enantiomers of a piperidone derivative (1) a solution of an optically active organic acid is placed in a suitable solvent at a certain temperature, optionally with the addition of catalytic amounts of a sulfonic acid, e.g., toluene- or camphorsulfonic acid. A solution of the mixture of enantiomers of the piperidone derivative (1) is slowly added to this temperature-controlled solution. The optically active organic acid, the solvent or mixture of solvents and the reaction temperature are selected so that the desired enantiomer of the piperidone derivative (1) crystallizes out as a salt of the optically active acid, whilst the other enantiomer remains in solution and racemizes under the reaction conditions. In this way, the desired enantiomer is constantly being formed and precipitated in a dynamic process until equilibrium is achieved.

The process according to the invention for dynamically separating the enantiomers of piperidone derivatives is thus characterized in that (a) an optically active acid and optionally catalytic amounts of a sulfonic acid are dissolved in a suitable solvent and this solution is kept at a specific temperature, (b) a solution of the piperidone derivative is slowly metered into this solution, so that the desired enantiomer crystallizes out as a salt of the organic acid used, while at the same time the unwanted isomer is racemized in solution and the content of desired enantiomer thus formed is also precipitated as a salt in a dynamic process, and (c) the salt of the desired enantiomer is separated off after crystallization has ended.

Suitable organic acids for the precipitation of the desired enantiomer include, for example, (+)- or (−)-ditoluoyltartaric acid or (+)- or (−)-dibenzoyltartaric acid. If desired, the reaction may be carried out in the presence of catalytic amounts of p-toluenesulfonic acid or camphorsulfonic acid. The reaction may be carried out, for example, in solvents such as acetone, acetonitrile, methanol, ethanol, n-propanol, isopropanol, tert-butanol, ethyl acetate, water, toluene, methylcyclohexane, n-butyl acetate or mixtures thereof. Preferably, acetonitrile or acetone is used.

By general formula (1)

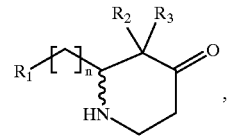

(1)

is meant a racemic or optically active mixture of enantiomers which consists of the two enantiomeric piperidone derivatives of general formulae (1a) and (1b)

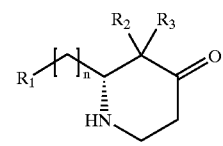

(1a)

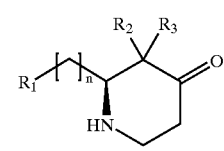

(1b)

A preferred process according to the invention is a process for isolating the enantiomer of general formula (1a)

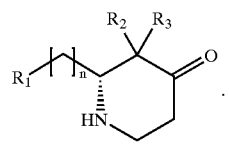

(1a)

The (+)-piperidone (1a) is precipitated, for example, by reaction with (+)-ditoluoyltartaric acid or (+)-dibenzoyltartaric acid and thus concentrated. With (−)-ditoluoyltartaric acid or (−)-dibenzoyltartaric acid, on the other hand, the opposite enantiomer is obtained, namely the (−)-piperidone (1b).

Particularly preferred is a process for obtaining the (+)-piperidone derivative of general formula (1a), wherein:

$R^1$ denotes 2-methoxyphenyl;

$R^2$ and $R^3$ each denote methyl; and n denotes 1, characterized in that the desired (R)-(+)-enantiomer is precipitated as the salt thereof by reacting with (+)-ditoluoyltartaric acid and at the same time, in the dissolved (S)-(−)-enantiomer, the chiral center is epimerized by heating to a temperature of about 30° C.-75° C., more preferably to 50° C.–65° C. The solvent used may be acetonitrile, acetone, or mixtures thereof, preferably acetonitrile.

Also preferred according to the invention is a process which leads to a piperidone of general formula (1a) or (1b) with an enantiomeric excess of ≧95% ee, more preferably ≧97% ee.

It is particularly preferred according to the invention to operate as follows: a mixture of the enantiomeric piperidone derivatives of general formula (1) is dissolved in an inert solvent, e.g., acetonitrile, and added slowly to a solution of a suitable tartaric acid derivative, preferably (+)-ditoluoyltartaric acid, in the same solvent, which has been heated to about 35° C. to 75° C., preferably to 50° C. to 65° C. Stirring is continued for a further 0.5 to 36 hours at the same temperature until there is no more precipitate being formed as far as the naked eye can tell. After cooling to ambient temperature, the crystals are suction filtered through a filter and the residue is washed with the cold solvent. After drying with gentle heating, the desired enantiomer is obtained in the form of the salt of the organic acid, from which the base can easily be liberated using known methods. The acid may be recovered in very good yields by simple extraction.

The separation of enantiomers of piperidone derivatives according to the invention by crystallization with simultaneous racemization of the unwanted enantiomer may be carried out starting from the free base of formula (1), which may also be used as the crude product containing up to 20% impurities, or starting from an acid addition salt precipitated to purify it, e.g., a hydrochloride or hydrobromide, after previous liberation of the base.

The high yield of 85% or more is certainly due to the following: the acidity of the acid used causes a racemization equilibrium to be achieved. Since the desired isomer is of low solubility as its salt, it is precipitated and is thus withdrawn from the equilibrium. By constant re-adjustment of the equilibrium, the mixture is finally converted almost entirely into the salt of the desired enantiomer which is of low solubility and is precipitated.

Unless otherwise stated, the terms listed below have the following meanings within the context of the present invention: the term alkyl, both on its own and in conjunction with other groups, denotes a straight-chain or branched alkyl group with the specified number of carbon atoms, such as, e.g., methyl, ethyl, n-propyl, isopropyl, n-butyl, tert-butyl, n-pentyl, or n-hexyl. Aryl denotes an aromatic hydrocarbon group having up to 10 carbon atoms, such as, for example, phenyl or naphthyl; heteroaryl denotes a mono- or bicyclic aromatic group having up to 10 ring atoms which comprises, in addition to carbon atoms, one or more heteroatom(s) which are selected independently of one another from among N, O, and S, such as, e.g., pyridine or furan. Halogen denotes fluorine, chlorine, or bromine.

The example which follows serves to illustrate one of the separation methods according to the invention, carried out by way of example, for obtaining enantiomerically pure piperidone derivatives of general formula (1). It should be regarded merely as a possible procedure, described by way of example, without restricting the invention to its contents.

EXAMPLE 1
(+)-(R)-2-(2-Methoxyphenyl)methyl-3,3-dimethyl-4-piperidonium hydrogenditoluoyltartrate 150 g (0.53 mol) of 2-(2-methoxyphenyl)methyl-3,3-dimethyl-4-piperidonium hydrochloride are first added to 320 ml of water. After the addition of 150 ml of toluene the pH is adjusted to 12.8 using 47.5 ml (0.53 mol) of sodium hydroxide solution (45% in water). The resulting mixture is stirred for about 40 minutes at ambient temperature with thorough mixing of the phases, left to stand, and then the aqueous phase is separated off. The organic phase is washed with 40 ml of water and then evaporated to dryness.

The oily residue (about 131 g, 0.53 mol) is dissolved in 131 ml of acetonitrile and measured into a solution of 204.2 g (0.53 mol) of (+)-ditoluoyltartaric acid in 102 ml of acetonitrile at 55° C.–60° C. over a period of 2 hours. After another 24 hours' stirring at this temperature the mixture is allowed to cool to ambient temperature over about 40 minutes and suction filtered through a filter. The residue is washed three times with 15 ml of acetonitrile and dried at 45° C.–50° C. in a drying cupboard until a constant weight is achieved. About 284 g (0.045 mol, 85%) of the title compound with an optical rotation of $\alpha_D^{20}$:+115° [c=2; MeOH] are obtained.

We claim:
1. A process for dynamically separating the enantiomers of a piperidone derivative of formula (1)

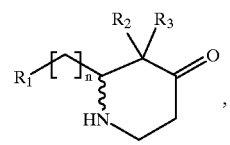

(1)

wherein:
$R_1$ is aryl optionally mono- to polysubstituted, heteroaryl, which is linked to the chiral center via at least one carbon atom of its own or a carbon atom belonging to the methylene bridge, or straight-chain or branched $C_1$–$C_8$-alkyl optionally mono- to polysubstituted by halogen;

$R_2$ and $R_3$, which are identical or different, are each straight-chain or branched $C_1$–$C_6$-alkyl; and n is 0, 1, 2 or 3, the process comprising:
(a) dissolving an optically active acid and optionally catalytic amounts of a sulfonic acid in a solvent to make a first solution maintained at a desired temperature;

(b) adding a second solution containing the piperidone derivative to the first solution to precipitate out the desired enantiomer of the piperidone derivative as a salt of the optically active acid while racemizing the unwanted enantiomer of the piperidone derivative in solution and further precipitating the desired enantiomer of the piperidone derivative formed from the racemization of the unwanted enantiomer of the piperidone derivative in solution; and (c) separating the desired enantiomer of the piperidone derivative as a salt of the optically active acid.

2. The process according to claim 1, wherein the desired enantiomer of the piperidone derivative of formula (1) has the formula (1a):

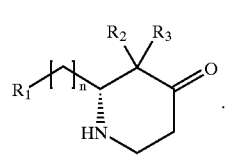

(1a)

3. The process according to claim 1, wherein:
$R_1$ is

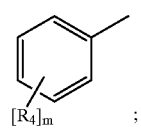

$R_2$ and $R_3$, which are identical or different, are each methyl or ethyl;

$R_4$ independently of one another are methoxy, ethoxy, isopropyloxy, halogen, hydroxy, $C_1$–$C_6$-alkyl, which is partially or fully halogenated, trifluoromethyl, amino, nitro, cyano, benzoyl, or $C_1$–$C_6$-alkylcarbonyl;

n is 1; and m is 0 or 1.

4. The process according to one of claims 1 to 3, wherein the optically active acid is ditoluoyltartaric acid or dibenzoyltartaric acid.

5. The process according to one of claims 1 to 3, wherein the optional sulfonic acid is toluenesulfonic acid or camphorsulfonic acid.

6. The process according to one of claims 1 to 3, wherein the solvent is selected from the group consisting of: acetone, acetonitrile, methanol, ethanol, n-propanol, isopropanol, tert-butanol, ethyl acetate, water, toluene, methylcyclohexane, n-butyl acetate, and mixtures thereof.

7. The process according to claim 6, wherein the solvent is selected from the group consisting of: acetone, acetonitrile, and mixtures thereof.

8. The process according to one of claims 1 to 3, wherein the process is carried out at a temperature of between 35° C. and 70° C.

9. The process according to one of claims 1 to 3, wherein the process is carried out at a temperature of between 50° C. and 65° C.

10. The process according to one of claims 1 to 3, wherein the desired enantiomer is obtained with a purity of ≧95% ee.

11. The process according to claim 1, wherein:

$R_1$ is 2-methoxyphenyl;

$R_2$ and $R_3$ are each methyl;

n is 1.

12. The process according to claim 1, wherein 1 equivalent of optically active acid is used.

13. The process according to claim 12, wherein the optically active acid is ditoluoyltartaric acid or dibenzoyltartaric acid.

14. The process according to claim 12, wherein the solvent is selected from the group consisting of: acetone, acetonitrile, methanol, ethanol, n-propanol, isopropanol, tert-butanol, ethyl acetate, water, toluene, methylcyclohexane, n-butyl acetate, and mixtures thereof.

15. The process according to claim 12, wherein the process is carried out at a temperature of between 35° C. and 70° C.

16. The process according to claim 15, wherein the process is carried out at a temperature of between 50° C. and 65° C.

17. The process according to claim 16, wherein the process is carried out at a temperature of between 55° C. to 60° C.

18. The process according to claim 12, wherein the optically active acid is ditoluoyltartaric acid, the solvent is acetone, and the process is carried out at a temperature of between 55° C. to 60° C.

19. The process according to claim 1, wherein a catalytic amount of a sulfonic acid is dissolved in the solvent in step (a).

20. The process according to claim 1, wherein:

$R_1$ is 2-methoxyphenyl;

$R_2$ and $R_3$ are each methyl or ethyl; and n is 1, wherein the first solution comprises 1 equivalent of ditoluoyltartaric acid in acetonitrile and the second solution comprises acetonitrile and wherein the process is carried out at a temperature of between 55° C. and 60° C.

21. The process according to claim 1, wherein:

$R_1$ is 2-methoxyphenyl;

$R_2$ and $R_3$ are each methyl; and n is 1, wherein the first solution comprises 1 equivalent of ditoluoyltartaric acid in acetonitrile and the second solution comprises acetonitrile and wherein the process is carried out at a temperature of between 55° C. and 60° C.

22. The process according to claim 2, wherein:

$R_1$ is 2-methoxyphenyl;

$R_2$ and $R_3$ are each methyl or ethyl; and n is 1, wherein the first solution comprises 1 equivalent of (+)-ditoluoyltartaric acid in acetonitrile and the second solution comprises acetonitrile and wherein the process is carried out at a temperature of between 55° C. and 60° C.

23. The process according to claim 2, wherein:

$R_1$ is 2-methoxyphenyl;

$R_2$ and $R_3$ are each methyl; and n is 1, wherein the first solution comprises 1 equivalent of (+)-ditoluoyltartaric acid in acetonitrile and the second solution comprises acetonitrile and wherein the process is carried out at a temperature of between 55° C. and 60° C.

* * * * *